(12) United States Patent
Clavel et al.

(10) Patent No.: US 9,388,226 B2
(45) Date of Patent: Jul. 12, 2016

(54) PEPTIDES MODULATING THE ACTIVITY OF MACROPHAGES, USEABLE FOR THE TREATMENT OF RHEUMATOID ARTHRITIS

(75) Inventors: Cyril Clavel, Plaisance du Touch (FR); Mireille Sebbag, Toulouse (FR); Maria Leonor Nogueira, Toulouse (FR); Guy Serre, Toulouse (FR)

(73) Assignee: Universite Paul Sabatier, Toulouse (FR)

( * ) Notice: Subject to any disclaimer, the term of this patent is extended or adjusted under 35 U.S.C. 154(b) by 1078 days.

(21) Appl. No.: 12/299,107

(22) PCT Filed: May 3, 2007

(86) PCT No.: PCT/FR2007/000758
§ 371 (c)(1),
(2), (4) Date: Mar. 11, 2009

(87) PCT Pub. No.: WO2007/125226
PCT Pub. Date: Nov. 8, 2007

(65) Prior Publication Data
US 2009/0298778 A1    Dec. 3, 2009

(30) Foreign Application Priority Data
May 3, 2006  (FR) ..................... 06 03956

(51) Int. Cl.
*A61K 38/10* (2006.01)
*C07K 14/47* (2006.01)
*C07K 7/08* (2006.01)
*A61K 38/00* (2006.01)

(52) U.S. Cl.
CPC ............. *C07K 14/4713* (2013.01); *A61K 38/10* (2013.01); *C07K 7/08* (2013.01); *A61K 38/00* (2013.01)

(58) Field of Classification Search
None
See application file for complete search history.

(56) References Cited

U.S. PATENT DOCUMENTS

| 2007/0009507 | A1  | 1/2007 | Serre et al. | |
| 2009/0028885 | A1* | 1/2009 | Serre ...................... | C07K 14/75 424/185.1 |
| 2013/0028922 | A1* | 1/2013 | Serre ...................... | C07K 14/75 424/185.1 |

FOREIGN PATENT DOCUMENTS

| WO | WO 99/34819 | 7/1999 |
| WO | WO 01/02437 A1 | 1/2001 |
| WO | WO 02/48180 A2 | 6/2002 |
| WO | WO 02/48181 A1 | 6/2002 |
| WO | WO 2006/048556 A1 | 5/2006 |
| WO | WO2006048556 A1 * | 5/2006 |

OTHER PUBLICATIONS

Sokolove et al. "Immune Complexes Containing Citrullinated Fibrinogen Costimulate Macrophages via Toll-like Receptor 4 and Fc_ Receptor." Arthritis & Rheumatism. vol. 63, No. 1, Jan. 2011, pp. 53-62.*
Ho et al. Autoimmunity against Fibrinogen Mediates Inflammatory Arthritis in Mice. The Journal of Immunology. vol. 184. pp. 379-390. 2010.*
Sokolove, Jeremy et al; "Immune complexes containing citrullinated fibreinogen costimulate macrophages via tole like receptor 4 and fcgammma receptor." Arthrits and rhematism (2011) 63(1) p. 53-62.*
Ho, Peggy P. et al; "Autoimmunity against fibrinogen mediates inflammatory arthritis in mice." J. Immunol. (2010) 184(1) p. 379-390.*
Singh, Bhagirath et al; "Minimum peptide sequences necessary for priming and triggering of humoral and cell mediated immune responses in mice: use of synthetic peptide antigens of defined structure." J. Immunol. (1980) 124(3) p. 1336-1344.*
Ruoslahti, Erkki; "RGD and other recognition sequences for integrins." Annu. Rev.Cell Dev. Biol. (1996) 12 p. 697-715.*
Sebbag, Mireille et al. "Clinical and pathophysiological signifance of autoimmune response to citrullinated proteins in rheumatoid arthritis" Joint Bone Spine, Elsevier, 71:493-502. 2004.
Vossenaar, Erik R. et al. "Rheumatoid arthritis specific anti-Sa antibodies target citrullinated vimentin" Arthritis Research & Therapy 6: R142-R150, 2004.
van Gaalen, Floris et al. "The Devil in the Details: The Emerging Role of Anticitrulline Autoimmunity in Rheumatoid Arthritis" Journal of Immunology, 175: 5575-5580, 2005.
Fournier, Catherine "Where do T Cells Stand in Rheumatoid Arthritis?" Joint Bone Spine, Elsevier, 72: 527-532, 2005.
Laurent et al., "Fcγ receptor profi le of monocytes and macrophages from rheumatoid arthritis patients and their response to immune complexes formed with autoantibodies to citrullinated proteins," Ann Rheum Dis, 70(6):1052-1059 (2011).
Iobagiu et al., "The antigen specificity of the rheumatoid arthritis-associated ACPA directed to citrullinated fibrin is very closely restricted," Journal of Autoimmunity, xxx:1-10 (2011).
Hida et al., "Influence of arginine deimination on antigenicity of fibrinogen," Journal of Autoimmunity 23:141-150 (2004).
Rubin et al., "The mouse immune response to human Wbrinogen reveals an autoimmune component against mouse Wbrinogen," Cellular Immunology 233:41-52 (2005).
Clavel et al., "Induction of macrophage secretion of tumor necrosis factor α through Fcγ receptor IIa engagement by rheumatoid arthritis-specific autoantibodies to citrullinated proteins complexed with fibrinogen," Arthritis & Rheumatism, 58(3):678-688 (2008).

* cited by examiner

*Primary Examiner* — Maury Audet
*Assistant Examiner* — Fred Reynolds
(74) *Attorney, Agent, or Firm* — Morgan, Lewis & Bockius LLP (57) ABSTRACT

The invention relates to citrulline peptides with anti-inflammatory properties. The invention also relates to an in vitro model for activation of macrophages, induced by immune complexes between specified IgG of rheumatoid arthritis and their citrulline targets.

8 Claims, 3 Drawing Sheets

PEPTIDES MODULATING THE ACTIVITY OF MACROPHAGES, USEABLE FOR THE TREATMENT OF RHEUMATOID ARTHRITIS

RELATED APPLICATIONS

The present application is a U.S. National Phase Application of International Application PCT/FR2007/000758, filed May 3, 2007, which claims the benefit of French Application No. 06/03956, filed May 3, 2006, all of which are herein incorporated by reference in their entirety.

The present invention relates to an if vitro model for macrophage activation induced by immune complexes between IgGs specific for rheumatoid arthritis (hereinafter abbreviated to "RA") and their citrullinated targets, and to the use thereof for identifying molecules having inflammation-modulating properties.

Rheumatoid arthritis is the most common of the chronic inflammatory rheumatisms. It is an autoimmune disease, and the serum of affected patients contains autoantibodies, some of which are specific, and can constitute a marker for this disease, allowing its diagnosis even at early stages. Research has therefore been carried out with a view to identifying antigens recognized by these antibodies, in order to obtain purified preparations therefrom that can be used in conventional techniques of immunological diagnosis.

It has been shown that RA-specific autoantibodies (IgGs) recognize various isoelectric variants of (pro)-filaggrin (for review, cf., for example, SERRE and VINCENT, in Autoantibodies, PETER and SHOENFELD Eds, Elsevier Science Publishers, 271-276, 1996). These autoantibodies have for this reason been named: "antifilaggrin autoantibodies (AFAs)". Application EP 0 511 116 describes the purification and characterization of antigens of the filaggrin family recognized by these antibodies, and the use thereof for the diagnosis of rheumatoid arthritis.

Subsequently, the filaggrin epitopes recognized by AFAs have been identified as regions of the filaggrin molecule bearing citrullyl residues, resulting from the conversion of arginyl residues by a peptidylarginine deiminase (Girbal Neuhauser E. et al., J. Immunol, 162, 585-94, 1999; Schellekens G A et al., J. Clin Invest, 101, 273-81, 1998). The analysis of various synthetic peptides derived from the human filaggrin sequence has shown that the deimination (citrullination) is necessary for making up the epitopes recognized by AFAs, which are today also called anti-citrullinated peptide autoantibodies (ACPAs).

A very large number of citrullinated peptides specifically recognized by ACPAs, and which can be used for diagnosing RA, have been obtained from filaggrin (application EP 0 929 669, application EP 1 475 438), and also other citrullinated proteins, among which mention will in particular be made of fibrin (application WO 01/02437) and vimentin (Vossenaar E R et al., Arthritis Res Ther 2004; 6:R142-R150).

In parallel, it has been shown that ACPAs are secreted by plasma cells of the synovial tissue (Masson-Bessière C et al., Clin Exp Immunol, 119, 544-52, 2000) and are specifically directed against citrullinated forms of the α- and β-chains of fibrin which are present in this tissue (Masson-Bessière C et al., J Immunol, 166, 4177-84, 2001).

The inventors have put forward the hypothesis that the formation of immune complexes (hereinafter abbreviated to "ICs") between ACPAs and the citrullinated epitopes specific for the latter, present in synovial tissue, play a role in the pathogenesis of rheumatoid arthritis and in particular in triggering and maintaining the inflammatory reaction, and that macrophages are very probably the principal effector cells of this reaction.

In order to validate this hypothesis, they have developed an in vitro model for macrophage activation induced by the interaction between the ICs formed from ACPAs and their citrullinated epitopes, and the macrophages.

This model, which mimics the physiopathological conditions of rheumatoid synovial tissue, implements the evaluation of the macrophage activation, after said macrophages have been brought into contact, in vitro, with ICs formed by ACPAs and citrullinated polypeptides recognized by said ACPAs.

The macrophage activation, which stimulates the production of pro-inflammatory cytokines, can be evaluated by assaying one or more of these cytokines (for example, TNF-α, IL-1β, IL-6, IL-8, GM-CSF, IL-15, etc.) in the culture supernatants of macrophages, after the latter have been brought into contact with said ICs.

This model is particularly suitable for evaluating the inflammation-modulating properties of a molecule, and especially its anti-inflammatory properties.

It can in particular be used for the in vitro identification of pharmacological agents capable of having an antagonistic effect on macrophage activation by ICs, either by opposing the formation of immune complexes between ACPAs and the citrullinated antigens recognized by said ACPAs, or by opposing the binding of said complexes to the macrophages.

The evaluation of the inflammation-modulating properties of a test molecule can be carried out simply, by comparing the production of one or more pro-inflammatory cytokines in the culture supernatants of macrophages activated by ICs, as described above, in the absence of the test molecule, and in the presence of the latter.

A subject of the present invention is a method for evaluating, in vitro, the inflammation-modulating properties of a molecule, characterized in that it comprises:

a) bringing anti-citrullinated peptide autoantibodies (AC-PAs) into contact with a citrullinated peptide antigen reactive with said ACPAs, under conditions which allow the formation of immune complexes between said ACPAs and said citrullinated antigen;

b) bringing the immune complexes formed in a) into contact with macrophages, under conditions which allow the activation of said macrophages by said immune complexes, and determining the amount of at least one pro-inflammatory cytokine produced by said macrophages;

c) repeating step a) and step b), one and/or the other of said steps being repeated in the presence of the test molecule;

d) comparing the amount of pro-inflammatory cytokine(s) produced in the absence of the test molecule and in the presence of the latter.

Advantageously, step a) is followed by a step for eliminating the IgGs which are not involved in the formation of immune complexes with the citrullinated antigen. These are, for example, free IgGs (which have not reacted with the citrullinated antigen at the end of step a)) or, where appropriate, IgGs possibly involved in the formation of immune complexes with the test molecule.

In this case, the citrullinated antigen will be immobilized on a solid support, such as microtitration plates or magnetic beads, in order to make it possible to readily carry out this elimination by rinsing.

The ACPAs that can be used for carrying out the method in accordance with the invention are, for example, IgGs obtained from a serum, or advantageously from a mixture of sera, of a patient or patients suffering from rheumatoid arthritis, and exhibiting a positive reaction to one or preferably more reference tests for detecting ACPAs (for example, the indirect immunofluorescence test on cryosections of rat esophagus described by Vincent C et al., Ann Rheum Dis 48, 712-22, (1989) or the ELISA assay on citrullinated human fibrinogen, described by Chapuy-Regaud S et al., Clin Exp Immunol, 139:542-50, 2005). Advantageously, said IgGs may also be purified by chromatography using a citrullinated antigen such as citrullinated fibrinogen, citrullinated filaggrin, citrullinated vimentin, etc. Use may also optionally be made of monoclonal ACPAs or ACPAs produced by genetic recombination.

The citrullinated antigen used for the formation of ICs with the ACPAs may be any citrullinated polypeptide or mixture of citrullinated polypeptides (natural or obtained by genetic recombination or chemical synthesis and then citrullination in vitro) capable of reacting with said ACPAs. This may in particular involve citrullinated filaggrin (application EP 0 511 116, application EP 0 929 669, application EP 1 475 438), citrullinated fibrin or fibrinogen (application WO 01/02437), citrullinated vimentin (Hill A et al., The Journal of Immunology, 2003, 171: 538-541; Vossenaar E R et al., Arthritis Res 2000, 2:429-432), or citrullinated fragments of these proteins capable of reacting with the ACPA preparation used. Those skilled in the art can readily verify, by means of basic immunological tests, the reactivity of a citrullinated antigen, whatever it is, with an ACPA preparation.

Advantageously, said citrullinated antigen comprises a citrullinated polypeptide derived from fibrin, chosen from those defined below, or a mixture of two or more of these polypeptides.

Preferably, the macrophages used are mammalian macrophages, in particular macrophages of human origin, which can be obtained, for example, from monocytes isolated using an anti-CD14 antibody, and differentiated into macrophages by culturing in the presence of M-CSF (macrophage-colony-stimulating factor).

In order to measure the macrophage activation, one (or optionally more) pro-inflammatory cytokine(s), preferably selected from TNF-α (tumor necrosis factor-α), interleukin-1β (IL-1β), interleukin-6 (IL-6), interleukin-8 (IL-8), GM-CSF (granulocyte macrophage-colony-stimulating factor) and interleukin-15 (IL-15), can be assayed. A preferred pro-inflammatory cytokine is TNF-α, which is abundantly produced by the macrophages of rheumatoid synovial tissue and which plays a major role in the inflammation and the destruction of joints (Feldmann M et al., Annu Rev Immunol 14:397-440, 1996).

The concentrations of ACPAs and of citrullinated peptide antigen which allow optimum formation of the immune complex, and optimum activation of the macrophages, can depend in particular on the ACPA preparation and on the peptide antigen preparation that are used. Those skilled in the art can readily determine the optimum reaction conditions by carrying out simple routine calibration tests, such as those described in the examples below.

A subject of the invention is also a pack (or kit) for carrying out a method in accordance with the invention, characterized in that it comprises a citrullinated peptide antigen optionally immobilized on a solid support, and anti-citrullinated peptide autoantibodies (ACPAs) capable of forming an immune complex with said antigen.

Said pack may also comprise means for assaying one or more pro-inflammatory cytokines.

Optionally, said pack also comprises M-CSF and a means for selecting monocytes, such as a support coated with anti-CD14 antibodies.

The subject of the present invention is also a method for selecting Inflammation-modulating molecules, characterized in that it comprises:
implementing, with each of the test molecules, a method for evaluating the inflammation-modulating properties of said molecule, as defined above,
selecting the molecules capable of modifying the amount of pro-inflammatory cytokine(s) produced by macrophages.

According to a preferred embodiment of a method of selection in accordance with the invention, it is a method for selecting anti-inflammatory molecules, and it comprises selecting the molecules capable of decreasing the amount of pro-inflammatory cytokine(s) produced by macrophages.

Anti-inflammatory molecules capable of decreasing the amount of pro-inflammatory cytokine(s) produced by macrophages during the implementation of a method in accordance with the invention can be used in particular for the preparation of medicaments for use in the treatment of inflammatory diseases involving immune complexes associating ACPAs and citrullinated antigens, and in particular of rheumatoid arthritis.

In this context, a subject of the present invention is also a citrullinated peptide capable of decreasing the amount of TNF-α produced by macrophages during the implementation of a method in accordance with the invention, for use as a medicament, especially for the treatment of inflammatory diseases, and in particular of rheumatoid arthritis.

Said peptide is selected from the group comprising the following peptides:
a peptide defined by the sequence $X_1$PAPPPISGGGY$X_2$A$X_3$ (SEQ ID NO: 1), in which $X_1$, $X_2$ and $X_3$ each represent a citrullyl residue or an arginyl residue, and at least one of the residues $X_2$ or $X_3$ is a citrullyl residue;
a peptide defined by the sequence GP$X_1$VVE$X_2$HQSACKDS (SEQ ID NO: 2) in which $X_1$ and $X_2$ each represent a citrullyl residue or an arginyl residue, and at least one of the residues $X_1$ or $X_2$ is a citrullyl residue;
a peptide defined by the sequence SGIGTLDGF$X_1$H$X_2$HPD (SEQ ID NO: 3) in which $X_1$ and $X_2$ each represent a citrullyl residue or an arginyl residue, and at least one of the residues $X_1$ or $X_2$ is a citrullyl residue;
a peptide defined by the sequence VDIDIKI$X_1$SC$X_2$GSCS (SEQ ID NO: 4) in which $X_1$ and $X_2$ each represent a citrullyl residue or an arginyl residue, and at least one of the residues $X_1$ or $X_2$ is a citrullyl residue;
a peptide defined by the sequence $X_1$GHAKS$X_2$PV$X_3$GIHTS (SEQ ID NO: 5) in which $X_1$, $X_2$ and $X_3$ each represent a citrullyl residue or an arginyl residue, and at least one of the residues $X_1$, $X_2$ or $X_3$ is a citrullyl residue;
a peptide comprising at least 5 consecutive amino acids, preferably at least 7 consecutive amino acids, and advantageously from 8 to 14 consecutive amino acids, at least one of which is a citrullyl residue, of one of the peptides above. In this case, said peptide preferably has a size of from 5 to 25 amino acids, and entirely preferably, a size of from 10 to 20 amino acids.

Advantageously, said peptide is selected from the group comprising the following peptides:
a peptide defined by the sequence SEQ ID NO: 1 in which at least $X_3$ is a citrullyl residue, or a peptide comprising a fragment of at least 5 consecutive amino acids of said sequence containing said citrullyl residue;

a peptide defined by the sequence SEQ ID NO: 2 in which at least $X_2$ is a citrullyl residue, or a peptide comprising a fragment of at least 5 consecutive amino acids of said sequence containing said citrullyl residue;

a peptide defined by the sequence SEQ ID NO: 3 in which at least $X_2$ is a citrullyl residue, or a peptide comprising a fragment of at least 5 consecutive amino acids of said sequence containing said citrullyl residue;

a peptide defined by the sequence SEQ ID NO: 4 in which at least $X_1$ is a citrullyl residue, or a peptide comprising a fragment of at least 5 consecutive amino acids of said sequence containing said citrullyl residue;

a peptide defined by the sequence SEQ ID NO: 5 in which at least $X_3$ is a citrullyl residue, or a peptide comprising a fragment of at least 5 consecutive amino acids of said sequence containing said citrullyl residue.

Particularly advantageously, said peptide is selected from the group consisting of:

a peptide defined by the sequence SEQ ID NO: 1 in which $X_1$, $X_2$ and $X_3$ are citrullyl residues, or a peptide of at least 16 amino acids comprising said sequence;

a peptide defined by the sequence SEQ ID NO: 2 in which $X_1$ and $X_2$ are citrullyl residues, or a peptide comprising a fragment of at least 5 consecutive amino acids of said sequence containing said citrullyl residues;

a peptide defined by the sequence SEQ ID NO: 3 in which $X_1$ and $X_2$ are citrullyl residues, or a peptide comprising a fragment of at least 5 consecutive amino acids of said sequence containing said citrullyl residues;

a peptide defined by the sequence SEQ ID NO: 4 in which $X_1$ and $X_2$ are citrullyl residues, or a peptide comprising a fragment of at least 5 consecutive amino acids of said sequence containing said citrullyl residues;

a peptide defined by the sequence SEQ ID NO: 5 in which $X_1$, $X_2$ and $X_3$ are citrullyl residues, or a peptide comprising a fragment of at least 10 consecutive amino acids of said sequence containing said citrullyl residues.

Very advantageously, said peptide is a peptide defined by the sequence SEQ ID NO: 1 in which $X_1$, $X_2$ and $X_3$ are citrullyl residues, or by the sequence SEQ ID NO: 2 in which $X_1$ and $X_2$ are citrullyl residues.

The citrullinated peptides that can be used as a medicament in accordance with the invention also encompass derivatives of the peptides SEQ ID NO: 1 to 5 or of the fragments thereof defined above, said derivatives bearing modifications intended to improve their recognition by the ACPAs: by way of examples of such derivatives, mention will be made of: cyclized peptides; peptides of retro type, in which the L-amino acids are linked together according to a sequence which is the reverse of that of the peptide to be reproduced; peptides of retro-inverso type, consisting of amino acids of the D series (instead of amino acids of the L series of natural peptides) linked together according to a sequence which is the reverse of that of the peptide to be reproduced.

Very advantageously, they are peptides in which the terminal carboxyl (COOH) function is replaced with a carboxamide ($CONH_2$) function. In this context, particularly preferred peptides are those in which the C-terminal residue is a citrullyl residue, the carboxyl function of which is replaced with a carboxamide function, for example in the case of the peptide defined by the sequence SEQ ID NO: 1, when at least $X_3$ is a citrullyl residue.

The citrullinated peptides that can be used as a medicament in accordance with the invention also encompass derivatives of the peptides SEQ ID NO: 1 to 5, or the fragments thereof as defined above, said derivatives bearing modifications intended to facilitate their synthesis and/or to improve their stability. By way of example of such derivatives, mention will be made of peptides including amino acids of which the carboxyl groups are esterified or converted to amide groups, and/or amino acids in which an amino group is alkylated, for example methylated or acetylated. The amine and carboxyl groups of the peptides may be present in the form of the salt corresponding to the base or to the acid.

From the citrullinated peptides described above, it is also possible to obtain mimotope peptides comprising at least one citrullyl residue (citrullinated mimotope peptide), that can also be used as medicaments in accordance with the invention.

These mimotope peptides can be obtained by synthesizing libraries of citrullinated peptides, the sequences of which are defined based on those of the peptides SEQ ID NO: 1 to 5, used in this context as "model peptides", and by carrying out the method in accordance with the invention, in order to evaluate the anti-inflammatory properties of these peptides.

Preferably, these peptide libraries are prepared by synthesizing various peptides of size between 10 and 20, preferably between 12 and 17 amino acids, in particular 15 amino acids. Each of these peptides conserves at least 2, preferably at least 4, advantageously at least 6, particularly preferably at least 8, and very advantageously at least 10 amino acids including at least one citrullyl residue, of the sequence of the model peptide chosen, at the same positions as on said model peptide, the other positions being variable.

Methods for synthesizing mimotope peptides are well known in themselves. Reference will, for example, be made to chapter 6 of "Chemical approaches to the synthesis of peptides and proteins", Paul Lloyd-Williams, Fernando Albericio and Ernest Giralt, CRC Press New York, 1997, "Peptides libraries", pages 237-270.

In accordance with the invention, the citrullinated peptides defined above can be used alone, in combination with one another, or, where appropriate, with other citrullinated peptides.

The subject of the present invention is thus pharmaceutical compositions, characterized in that they comprise, as active ingredient, at least one citrullinated peptide as defined above.

Compositions in accordance with the invention may, for example, combine between them various citrullinated peptides chosen from those defined above, or else may combine one or more of said peptides, with one or more citrullinated peptides derived in particular from filaggrin.

According to a preferred embodiment of a pharmaceutical composition in accordance with the invention, it comprises at least one peptide of sequence SEQ ID NO: 1, and at least one peptide of sequence SEQ ID NO: 2, as defined above, and it may optionally also comprise a peptide of sequence SEQ ID NO: 3 and/or a peptide of sequence SEQ ID NO: 4 and/or a peptide of sequence SEQ ID NO: 5, as defined above.

Pharmaceutical compositions in accordance with the invention may also comprise excipients or additives normally used in pharmacy.

The invention will be understood more clearly from the figures and nonlimiting examples which follow and which are given here for the purpose of illustration.

EXAMPLE 1

In Vitro Evaluation of the Pro-inflammatory Effect of Immune Complexes Associating Citrullinated Fibrinogen and ACPAs The present example concerns the preparation of the model for in vitro macrophage stimulation with immune complexes formed from ACPAs and from citrullinated epitopes which are reactive with said ACPAs.

Monocytes are purified from blood mononuclear cells of normal individuals using an anti-CD14 antibody coupled to magnetic beads. These monocytes are differentiated to macrophages by culturing for 7 days in the presence of M-CSF, and are then stimulated with immobilized ICs.

The latter are reconstituted by reacting ACPAs purified from sera of patients suffering from RA, on citrullinated human fibrinogen adsorbed at the bottom of a culture plate. The macrophage activation is assessed through their secretion of TNF-α, assayed in the culture supernatants after 24 h of contact.

The technical details which made it possible to prepare this macrophage stimulation model are described below.

Macrophage Preparation:

Using samples of blood or leucocyte concentrates from normal individuals (Établissement Français du Sang [French Blood Bank], Toulouse, France), the mononuclear cells are separated from the debris and other blood cells by centrifugation for 20 min at 1200 g on Ficoll (Ficoll 400®, Biocoll isoton separating solution, 1.077 g/ml, Biochrom AG, Berlin, Germany) at a rate of 15 ml of Ficoll per 30 ml of cell suspension diluted 50/50 in PBS (phosphate buffered saline) at pH 7.4, containing 0.1% of serum albumin (BSA, Sigma-Aldrich Chimie, St Quentin Fallavier, France) and 0.6% of sodium citrate (this solution will subsequently be referred to as PBNaCit). After 2 washes with 25 ml of PBNaCit, the viable cells are counted using a counting cell after staining with 0.4% Trypan blue. Positive sorting of cells of the monocyte line (expressing the CD14 marker) is carried out using an anti-human CD14 antibody coupled to magnetic beads (CD14 MicroBeads, Miltenyi Biotec, Paris, France). A mixture adhering to a proportion of 140 µl of anti-CD14 antibodies and 1200 µl of PBNaCit per 140×10$^6$ mononuclear cells is incubated for 15 minutes at 4° C. After washing with 25 ml of PBNaCit, the cell suspension is loaded onto a column containing ferromagnetic beads (MS column, Miltenyi Biotec), conditioned with 1 ml of PBNaCit and placed in a magnetic field. After 3 washes with 500 µl of PBNaCit for eliminating the cells not expressing CD14, the column is removed from the magnetic field and the cells labeled with the anti-CD14 antibody are flushed with 500 µl of PBNaCit. The viable cells are counted using a counting cell after staining with 0.4% Trypan blue. The monocytes are subsequently cultured at 10$^6$ viable cells/ml in macrophage-SFM medium (serum-free medium designed for the culture of human peripheral monocytes and macrophages, Gibco, Invitrogen, Cergy Pontoise, France), supplemented with fetal calf serum (10%, v/v, Biowest, Nuaillé, France) and with M-CSF (Macrophage Colony Stimulating Factor) at 100 ng/ml (Peprotech, Levallois-Perret, France) in Teflon wells, for 7 days at 37° C. under an atmosphere containing 5% $CO_2$. At the end of this incubation, macrophages are obtained. The latter are washed in macrophage-SFM medium and the viable cells are then counted using a counting cell after staining with 0.4% Trypan blue.

Citrullination (Deimination) of Human Fibrinogen

The residual contaminating IgGs are removed from a commercially available preparation of purified human fibrinogen, (Calbiochem, Meudon, France) by affinity chromatography on a protein G column (HiTrap Protein G, GE Healthcare, Orsay, France) according to the conditions recommended by its manufacturer. The fibrinogen is subsequently incubated for 2 hours at 37° C. in a 0.1M Tris-HCl buffer, pH 7.4, containing 10 mM $CaCl_2$ and 5 mM dithiothreitol and in the presence or absence of rabbit skeletal muscle peptidylarginine deiminase (Sigma-Aldrich) at a rate of 7 U of enzyme/mg of fibrinogen. The various chains constituting the fibrinogen, associated following the incubation in this disulfide-bridge-reducing buffer, are subsequently reassociated by a dialysis against PBS, carried out until complete reassociation of the various chains, verified by SDS-PAGE under nonreducing conditions, has been obtained. Two fibrinogen preparations are thus obtained: citrullinated (incubated in the presence of enzyme) and noncirullinated (incubated in the absence of enzyme).

Preparation of Heat-Aggregated Human IgGs

The soluble aggregated human IgGs (hereinafter referred to as aggregated IgGs) are prepared by incubating, at 63° C. for 20 minutes, a solution of purified human IgGs from normal individuals (Sigma-Aldrich) at 2 mg/ml in PBS. After centrifugation at 12000 g, the supernatant containing the soluble aggregated human IgGs is recovered and used extemporaneously.

Preparation of a Mixture of ACPA-Positive IgGs

A mixture of ACPA-positive IgGs (hereinafter referred to as IgG ACPA+) is prepared by isolating the IgG fraction of an equal-parts mixture of 38 sera from patients suffering from RA, having a high serum ACPA titer, by affinity chromatography on a 5 ml protein G column (HiTrap Protein G, GE Healthcare, Orsay, France). After equilibration of the column in 0.02M $KH_2PO_4/K_2HPO_4$ buffer, pH 7.0, 40 ml of mixture of sera diluted to 1/4 in this same buffer and passed through a 0.22 µm filter are loaded onto the column at a rate of 2 ml per minute. After the column has been washed with 5 volumes of 0.02M $KH_2PO_4/K_2HPO_4$, pH 7.0, containing 1M of NaCl, the total IgG ACPA+ are eluted in glycine-HCl buffer at 0.2M, pH 2.7. The elution fractions are immediately placed at neutral pH by adding 2M Tris. The fractions richest in IgGs are detected by monitoring the optical density at 280 nm (Biophotometer Eppendorf, Eppendorf, Dominique Dutscher, Brumath, France), combined and dialyzed against 0.02M $KH_2PO_4/K_2HPO_4$, pH 7.0, containing 0.5M of NaCl, passed through a 0.22 µm filter and then aliquoted and stored at −20° C. until use. The quality of the purification is verified by staining with Coomassie blue after electrophoresis on a PHAST-system automat (GE Healthcare, Orsay, France) in an SDS-12.5% PAGE gel.

Preparation of a Mixture of ACPA-Negative IgGs

A mixture of ACPA-negative IgGs (hereinafter referred to as control IgGs) is prepared by isolating the IgG fraction of an equal-parts mixture of 20 human sera, all having a zero titer after assaying of the ACPAs by means of two reference assays, indirect immunofluorescence on cryosections of rat esophagus Vincent C et al., Ann Rheum Dis 48, 712-22, 1989) and ELISA on human citrullinated fibrinogen (Chapuy-Regaud S et al., Clin Exp Immunol, 139:542-50, 2005). The isolation of the IgG fraction is carried out by affinity chromatography on a protein G column exactly according to the protocol used to prepare the IgG ACPA+.

Reconstitution of Immune Complexes (ICs) Associating ACPAs and Citrullinated Fibrinogen:

The reconstitution of ICs associating ACPAs and citrullinated fibrinogen is carried out by coating flat-bottomed 96-well culture plates (Nunclon delta, Nunc, Roskilde, Denmark), under sterile conditions, with human citrullinated fibrinogen at 10 µg/ml, added at a rate of 50 µl/well and incubated overnight at 4° C. The plates are subsequently saturated in PBS, pH 7.4, 2% BSA for 1 hour at 4° C. (180 µl/well). After 3 washes in PBS, pH 7.4, 0.1% Tween-20, the wells are incubated for 2 hours at 4° C. with 100 µl of IgG ACPA+ at various concentrations (ranging from 9 to 0.28 mg/ml) diluted in PBS containing 2% BSA and 2M NaCl. Negative controls are made up in the same way, using either noncitrullinated human fibrinogen as antigen coated at the bottom of the plate, or control IgGs as antibodies. Wells coated only with citrullinated or noncitrullinated human fibrinogen and saturated in PBS, pH 7.4, 2% BSA are also used as negative controls.

Macrophage Stimulation:

After 3 washes in PBS, pH 7.4, 0.1% Tween-20, then 3 washes in PBS, the macrophages are added at a rate of 50000 viable cells/well in a volume of 200 µl. After incubation for 24 hours at 37° C. under an atmosphere containing 5% $CO_2$, the supernatants are recovered (160 µl/well) and are rapidly frozen at −20° C. until they are analyzed. The negative control for activation is carried out using macrophages in macrophage-SFM medium alone. Macrophages placed on aggregated IgGs immobilized at the bottom of the culture plates by passive adsorption (at a rate of 100 µl of a solution at 5 µg/ml per well), or placed in the presence of bacterial lipopolysaccharide (LPS, *Escherichia coli* 0.55:B5 at a final concentration of 0.5 µg/ml; Sigma-Aldrich Chimie), are used as controls for the ability of the macrophages to respond to a stimulus inducing TNF-α synthesis.

Assaying TNF-α in the Culture Supernatants

An ELISA assay kit for human TNF-α, comprising a capture antibody, a detection antibody and recombinant human TNF-α for making up a calibration range of 7.8 to 500 pg/ml, was used to assay this cytokine in the culture supernatants (Human TNF-alpha BD OptEIA™ ELISA et, BD Biosciences Pharmingen, Pont-de-Claix, France).

Figure 1:
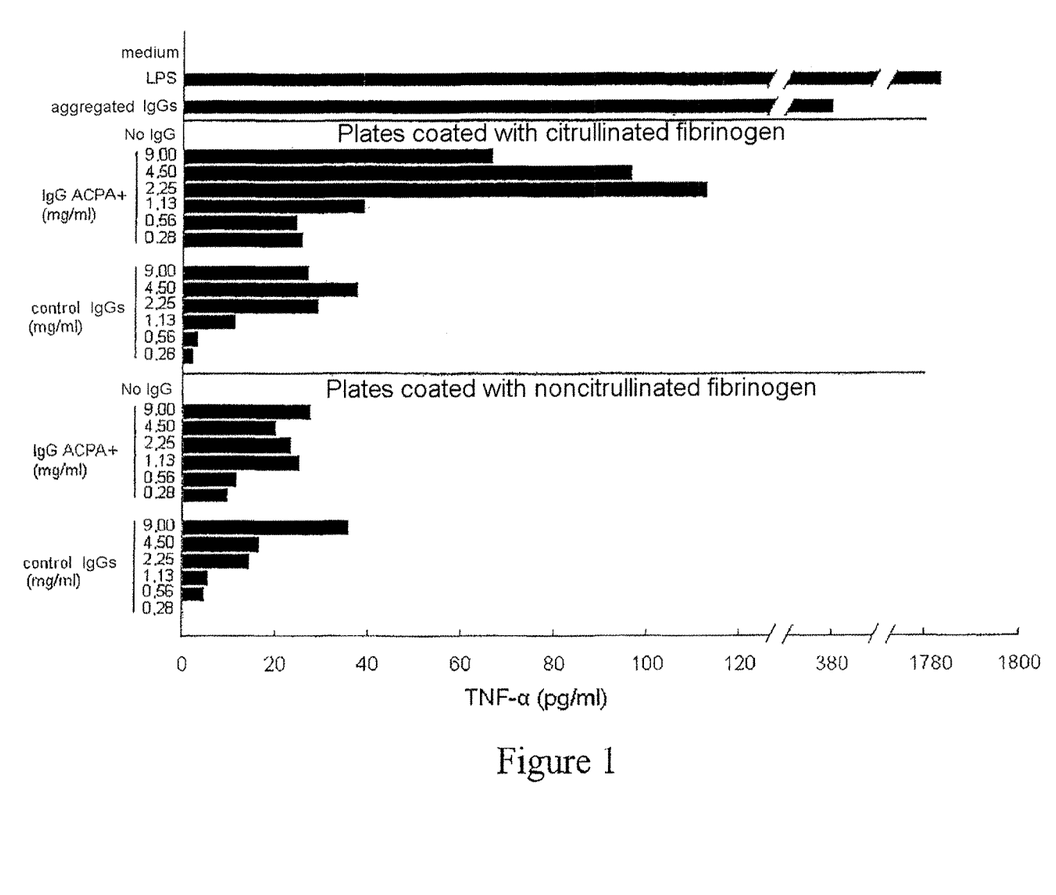
FIG. 1: Measurement of the amount of TNF-α (pg/ml) secreted by macrophages in the presence of citrullinated or noncitrullinated fibrinogen, and of various concentrations (0, 0.28, 0.56, 1.13, 2.25, 4.50 and 9.00 mg/ml) of ACPAs (IgG ACPA+), or of control IgGs. The amount of TNF-α is also measured with the macrophages placed in the presence of heat-aggregated IgGs (aggregated IgGs), or of bacterial lipopolysaccharide (LPS), or left in macrophage-SFM medium alone (medium).

Results:

The results obtained are illustrated in FIG. 1. These data are representative of the result of 7 different experiments out of a total of 10 experiments carried out with the macrophages of different individuals.

Nonspecific attachment of control IgGs to the citrullinated or noncitrullinated fibrinogen and of the IgG ACPA+ to the noncitrullinated fibrinogen makes it possible to induce a basal level of TNF-α synthesis of less than 40 pg/ml. This stimulation is very much increased when specific ICs are reconstituted following the interaction of the IgG ACPA+ with the citrullinated fibrinogen, when concentrations of IgG ACPA+ of greater than 1.13 mg/ml are used. A maximum stimulation is observed for an IgG ACPA+ concentration of 2.25 mg/ml and the TNF-α level reaches a value close to 120 pg/ml.

It should be noted that, whatever the IgGs used, the TNF-α induction increases when increasing concentrations of IgG are used, and subsequently decreases in an equally dose-dependent manner ("bell-shaped curve" effect). This leads one to assume that, beyond a certain concentration of immobilized IgGs, pathways exerting a negative-regulation effect on TNF-α production are activated.

As expected, the stimulation with the IC substitutes constituted by the heat-aggregated human IgGs induces a large production of TNF-α. Very large amounts of TNF-α are also produced in response to LPS.

This cellular and molecular model of entirely human origin makes it possible to demonstrate the pro-inflammatory effect of the interaction between macrophages and ICs associating citrullinated fibrinogen and ACPAs, since these complexes reconstituted in vitro specifically induce TNF-α production by these cells (FIG. 1). This production is in fact clearly increased compared with that which is observed after bringing into contact with IgGs of any specificity, probably immobilized on the culture plates following nonspecific binding to the citrullinated or noncitrullinated fibrinogen. It is also dependent on the amount of IgG ACPA+ added, making it possible to define an optimum concentration promoting the formation of activating ICs.

EXAMPLE 2

Inhibition of the Reactivity of IgG ACPA+ with Respect to Citrullinated Fibrinogen by Fibrinogen-Derived Citrullinated Peptides Bearing Epitopes Recognized by the ACPAs The inventors have identified several fibrin-derived citrullinated peptides bearing epitopes specifically recognized by ACPAs.

These peptides are listed in table 1.

The standard one-letter code for amino acid residues is used. X indicates a citrullyl residue.

The nomenclature used is the following: name of origin of the polypeptide chain (α or β) of fibrinogen from which the sequence derives, then position, in this sequence, of the amino-terminal residue of the peptide—position of the carboxy-terminal residue of the peptide. These positions are numbered with respect to the N-terminal end of the fibrinogen chains (signal peptide included). The notation cit indicates that it is a citrullinated form of the peptide. The position of the arginyl residue which is substituted with a citrullyl residue is indicated as a suffix. The nomenclature for the noncitrullinated forms of the peptides is the same, except that the notation cit and the position of the arginyl residues are omitted. The peptide $\beta 60\text{-}74cit_{60, 72, 74}$ has an animated C-terminal function (carboxamide function: $CONH_2$).

TABLE 1

| PEPTIDE NAME | SEQUENCE |
|---|---|
| $\alpha 36\text{-}50cit_{36, 42}$ | GPXVVEXHQSACKDS (SEQ ID NO: 6) |
| $\alpha 171\text{-}185cit_{178, 181}$ | VDIDIKIXSCXGSCS (SEQ ID NO: 7) |

TABLE 1-continued

| PEPTIDE NAME | SEQUENCE |
|---|---|
| α183-197cit$_{1156, 190}$ | SCSXALAXEVDLKDY (SEQ ID NO: 8) |
| α246-260cit$_{258}$ | PEWKALTDMPQMXME (SEQ ID NO: 9) |
| α259-273cit$_{263, 271}$ | MELEXPGGNEITXGG (SEQ ID NO: 10) |
| α366-380cit$_{367}$ | EXGSAGHWTSESSVS (SEQ ID NO: 11) |
| α396-410cit$_{404}$ | DSPGSGNAXPNNPDW (SEQ ID NO: 12) |
| α411-425cit$_{425}$ | GTFEEVSGNVSPGTX (SEQ ID NO: 13) |
| α501-515cit$_{510, 512}$ | SGIGTLDGFXHXHPD (SEQ ID NO: 14) |
| α546-560cit$_{547}$ | SXGSESGIFTNTKES (SEQ ID NO: 15) |
| α561-575cit$_{573}$ | SSHHPGIAEFPSXGK (SEQ ID NO: 16) |
| α588-602cit$_{591}$ | SYNXGDSTFESKSYK (SEQ ID NO: 17) |
| α621-635Cit$_{621, 627, 630}$ | XGHAKSXPVXGIHTS (SEQ ID NO: 18) |
| β60-74cit$_{80, 72, 74}$ | XPAPPPISGGGYXAX (SEQ ID NO: 19) |
| β210-224cit$_{224}$ | QKLESDVSAQMEYCX (SEQ ID NO: 20) |
| β281-295cit$_{285, 294}$ | VIQNXQDGSVDFGXK (SEQ ID NO: 21) |
| β420-434cit$_{421}$ | PXKQCSKEDGGGWWY (SEQ ID NO: 22) |
| β433-447cit$_{436, 445}$ | WYNXCHAANPNGXYY (SEQ ID NO: 23) |

Among these peptides, those which bear immunodominant epitopes (recognized by a large number of sera from patients suffering from RA) are given in table 2. The 20 sera tested correspond to a series originating from patients suffering from RA having ACPAs detectable by means of multiple tests for detecting these autoantibodies and which, taken as a whole, make it possible to represent the heterogeneity of the specificity profiles encountered in the patients.

TABLE 2

| PEPTIDE NAME | NUMBER OF REACTIVE SERA OUT OF THE 20 TESTED |
|---|---|
| β60-74cit$_{60, 72, 74}$ | 14 |
| α36-50cit$_{38, 42}$ | 12 |
| α621-635cit$_{621, 627, 630}$ | 10 |
| α501-515cit$_{510, 512}$ | 9 |
| α171-185cit$_{178, 181}$ | 9 |

The present example shows the ability of two of these immunodominant peptides (α36-50cit$_{38, 42}$ and β60-74cit$_{60, 72, 74}$) to inhibit the immunoreactivity of ACPAs with respect to citrullinated human fibrinogen, measured by ELISA.

The technical details of this competition assay by the ELISA method are indicated below.

96-well microtitration plates (MaxiSorp, Nunc, VWR International, Fontenay sous Bois, France) are coated with citrullinated human fibrinogen (prepared as indicated in example 1) at a rate of 100 μl/well of a solution at 5 μg/ml in PBS, pH 7.4, overnight at 4° C. The plates are then saturated with a solution of PBS containing 2% of BSA (PBS-2% BSA) (180 μl/well). After this step, the IgG ACPA+ (prepared as indicated in example 1), diluted beforehand to 16 μg/ml in PBS-2% BSA in the presence or absence of increasing amounts of the competitor peptides α36-50cit$_{38, 42}$ and/or β60-74cit$_{60, 72, 74}$ (each at a concentration ranging from 0.006 to 1.56 mg/ml) added 2 h before the ELISA assay, are added. The concentration used for the IgG ACPA+ was chosen because it makes it possible to obtain an OD of between 1 and 1.5 in the absence of competitor peptide. Citrullinated or noncitrullinated fibrinogen (0.0002 to 1.56 mg/ml) and the noncitrullinated forms of the α36-50cit$_{38, 42}$ and β60-74cit$_{60, 72, 74}$ peptides (respectively referred to as α36-50 and β60-74) are used as control. The ACPA binding is then detected with peroxidase-labeled anti-human IgG goat IgGs (SouthernBiotech, Birmingham, Ala.) diluted to 1/9000 in PBS-2% BSA. All the incubations are carried out for 1 h at 4° C. and are followed by washes in PBS-0.1% Tween 20. The peroxidase activity is revealed with a solution of ortho-phenylenediamine (2 mg/ml—Sigma-Aldrich) in hydrogen peroxide (0.03%—Sigma-Aldrich) and the OD at 492 nm is measured using a plate reader (Multiskan plate reader, Thermo Labsystem, Cergy-Pontoise, France).

Figure 2:
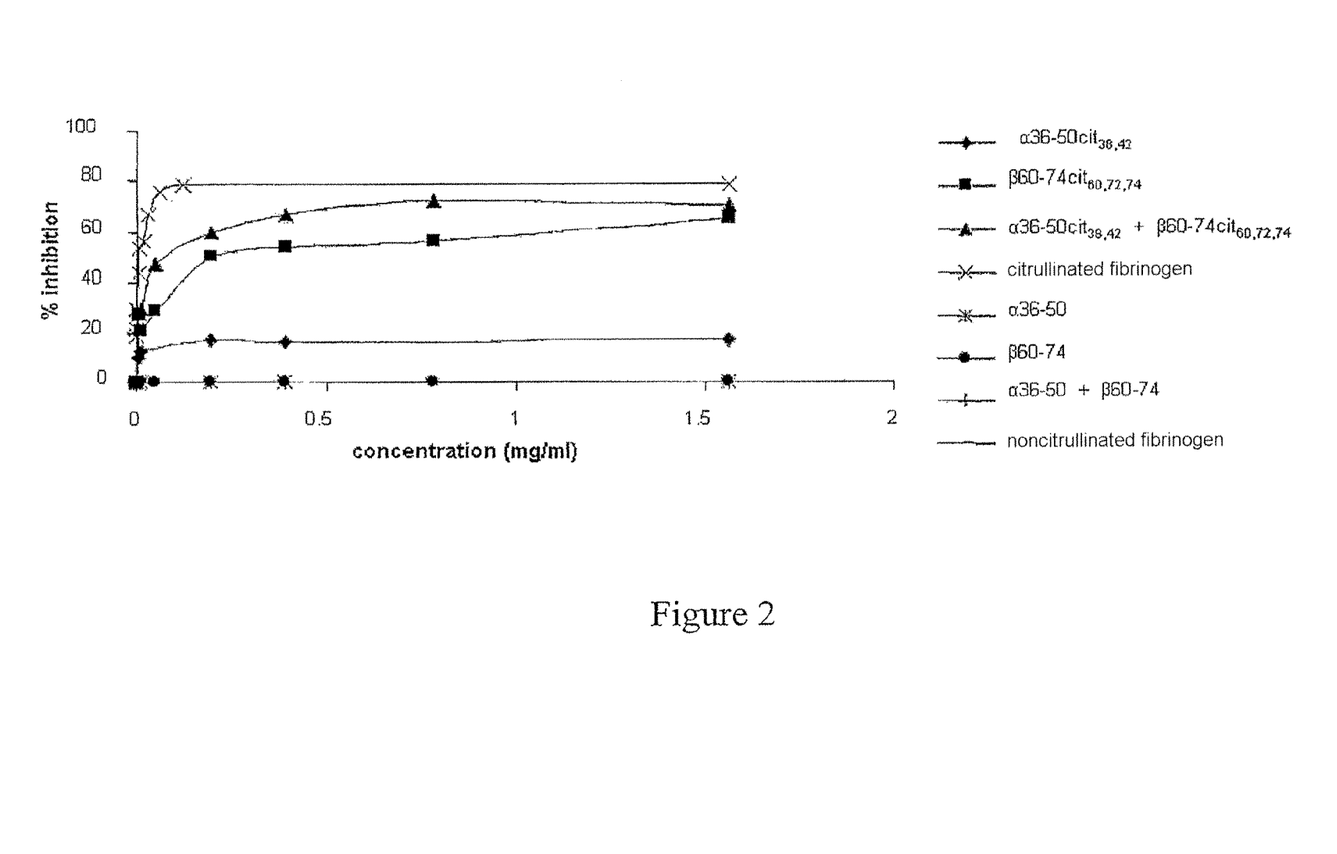
FIG. 2: Effect of increasing concentrations (from 0.006 to 1.56 mg/ml) of citrullinated fibrinogen (cross) or noncitrullinated fibrinogen (line), of α36-50Cit$_{38, 42}$ peptide (diamond), of α36-50 peptide (6-branch cross), of β60-74Cit$_{60, 72, 74}$ peptide (square), of β60-74 peptide (circle), of a mixture of α36-50Cit$_{38, 42}$ and β60-74Cit$_{63, 72, 74}$ peptides (triangle) or of a mixture of α36-50 and β60-74 peptides (vertical line) on the percentage inhibition of the reactivity of the ACPA+ with respect to citrullinated fibrinogen.

Results:

The results of this ELISA competition assay are illustrated in FIG. 2. The data are representative of 3 experiments carried out with two different preparations of IgG ACPA+. The results are expressed as degree of inhibition of the reactivity obtained in the absence of competitor peptide.

The percentage inhibition of the ACPA binding to the citrullinated fibrinogen attached to the ELISA plate reaches a plateau value of approximately 80% with the citrullinated fibrinogen, of approximately 70% with the α36-50cit$_{38, 42}$+β60-74cit$_{60, 72, 74}$ mixture, of approximately 60% with β60-74cit$_{60, 72, 74}$ and of approximately 15% with α36-50cit$_{38, 42}$. The percentage inhibition is zero with the same molecules which have not been citrullinated.

These results confirm that the fibrin-derived citrullinated peptides α36-50cit$_{38, 42}$ and β60-74cit$_{60, 72, 74}$ bear major epitopes recognized by ACPAs since they are capable of inducing a significant inhibition of the reactivity of a heterogeneous mixture of ACPAs with respect to citrullinated fibrinogen immobilized at the bottom of ELISA plates. This inhibition is increased when the mixture of these two peptides is used, confirming that both are recognized by different subfamilies of ACPAs.

EXAMPLE 3

Inhibition of the Stimulation of Human Macrophages by ICs Associating ACPAs and Citrullinated Fibrinogen, Using Fibrinogen-Derived Citrullinated Peptides Bearing Epitopes Recognized by ACPAs The preparation and the stimulation of the macrophages are carried out exactly under the conditions described in example 1, except for the fact that the reconstitution of ICs is carried out with IgG ACPA+ diluted to 1.13 mg/ml in PBS containing 2M of NaCl and 2% of BSA in the presence or absence of the competitor peptide β60-74cit$_{60, 72, 74}$ at two concentrations (0.8 and 4 mg/ml) added 2 h before the incubation with the citrullinated fibrinogen immobilized at the bottom of the culture plates. Competitions with citrullinated or noncitrullinated fibrinogen (0.4 mg/ml) and also with the noncitrullinated peptide β60-74 (0.8 and 4 mg/ml), are also carried out as control.

Figure 3:
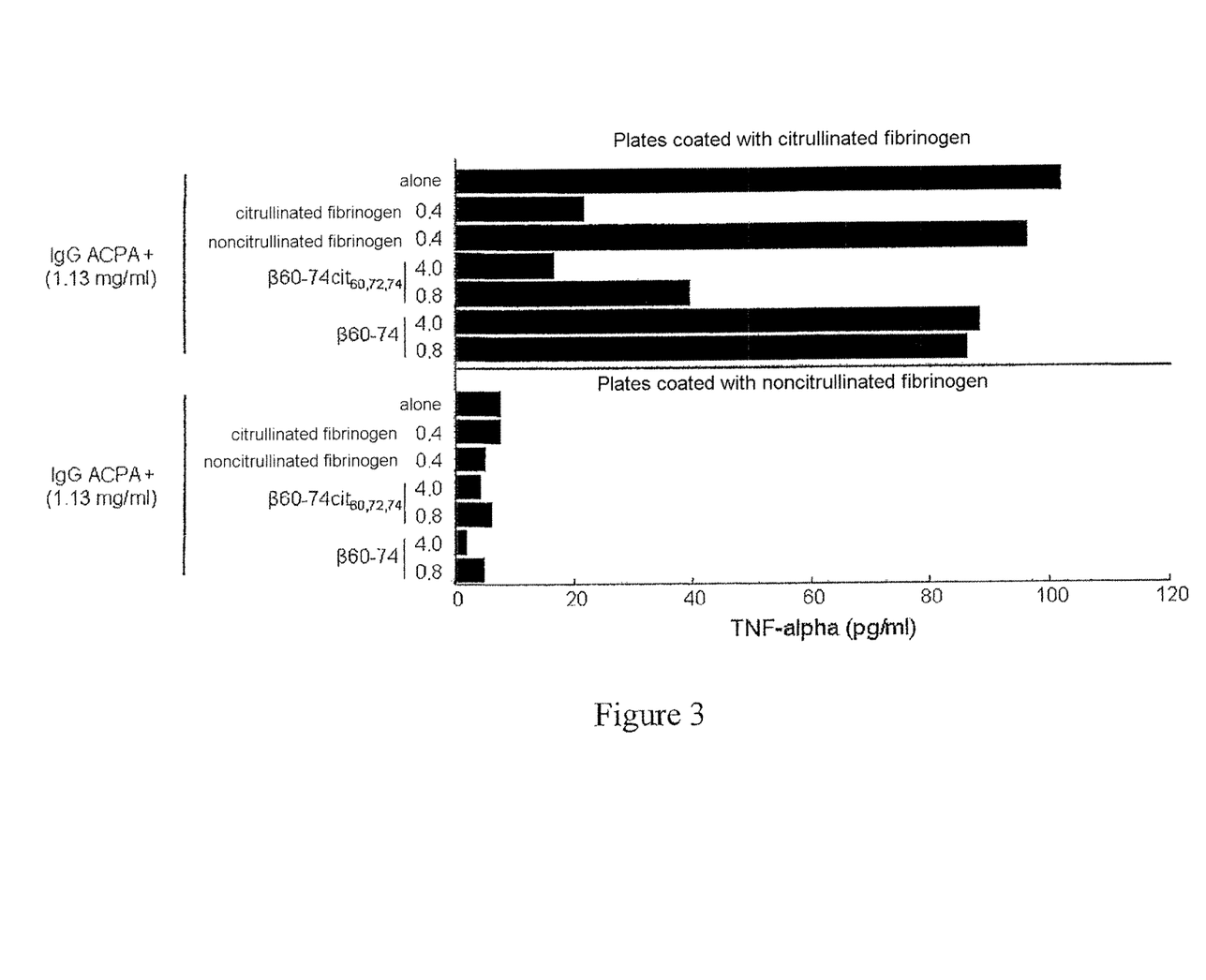
FIG. 3: Measurement of the amount of TNF-α (pg/ml) secreted by macrophages placed in the presence of citrullinated fibrinogen or noncitrullinated fibrinogen control) and of 1.13 mg/ml of IgG ACPA+ and in the presence or absence of the following competitors: citrullinated or noncitrullinated fibrinogen (4.0 mg/ml), β60-74Cit$_{40, 72, 74}$ peptide or β60-74 peptide (0.8 or 4.0 mg/ml).

Results:

The results of this inhibition assay are illustrated in FIG. 3. These data are representative of the result of 2 different experiments carried out with the macrophages from 2 different individuals.

Incubation of the plates coated with noncitrullinated fibrinogen, with IgG ACPA+ alone or in the presence of the citrullinated or noncitrullinated molecules, followed by stimulation of the macrophages, makes it possible to define a basal level of TNFα of less than 10 pg/ml. This stimulation is increased when the plates coated with citrullinated fibrinogen are incubated with the IgG ACPA+ alone or in the presence of the noncitrullinated molecules, and the TNFα level reaches values of greater than 80 pg/ml. This stimulation is less when the ACPAs+ are placed in the presence of citrullinated fibrinogen (approximately 20 pg/ml) or of the β60-74 $cit_{60, 72, 74}$ peptide (less than 20 pg/ml for a citrullinated peptide concentration of 4 mg/ml and approximately 40 pg/ml for a citrullinated peptide concentration of 0.8 mg/ml).

These results show that the β60-74$cit_{60, 72, 74}$ peptide induces dose-dependent inhibition of TNF-α production in response to the ICs. The same result is observed when citrullinated fibrinogen is used as competitor. On the other hand, the noncitrullinated forms of the peptide and of fibrinogen have no inhibitory effect.

These results indicate that the fibrin-derived citrullinated peptide β60-74$cit_{60, 72, 74}$ is capable of preventing the formation of immobilized ICs associating ACPAs and citrullinated fibrinogen. This results in inhibition of TNF-α production in response to these ICs.

The invention claimed is:

1. A method for reducing levels of immune complexes between anti-citrullinated protein autoantibodies (ACPAs) and citrullinated fibrinogen, wherein said method comprises administering a citrullinated peptide to a subject suffering from rheumatoid arthritis, with the citrullinated peptide being selected from the group consisting of:
   (a) a peptide having the sequence $X_1$PAPPPISGGGY$X_2$A$X_3$ (SEQ ID NO: 1) in which $X_1$ and $X_2$ each represent a citrullyl residue or an arginyl residue, and $X_3$ is a citrullyl residue, and
   (b) a peptide of 5 to 25 amino acids, said peptide comprising a fragment of at least 5 consecutive amino acids of the peptide of SEQ ID NO:1, said fragment of SEQ ID NO:1 containing at least a citrullyl residue at $X_3$.

2. The method as claimed in claim 1, further comprising administering to said subject a citrullinated peptide selected from the group consisting of:
   a peptide defined by the sequence GP$X_1$VVE$X_2$HQSACKDS (SEQ ID NO: 2) in which $X_1$ and $X_2$ each represent a citrullyl residue or an arginyl residue, and at least one of the residues $X_1$ or $X_2$ is a citrullyl residue, and a peptide of 5 to 25 amino acids, said peptide comprising a fragment of at least 5 consecutive amino acids of the peptide of SEQ ID NO:2, wherein the fragment comprises at least one of $X_1$ and $X_2$ as a citrullyl residue.

3. The method as claimed in claim 1, wherein said citrullinated peptide is selected from the group consisting of:
   (a) a peptide of sequence SEQ ID NO: 1 in which at least $X_2$ and $X_3$ are citrullyl residues, and
   (b) a peptide of 5 to 25 amino acids, said peptide comprising a fragment of at least 5 consecutive amino acids of the amino acid sequence of SEQ ID NO:1, said fragment comprising citrullyl residues at $X_2$ and $X_3$.

4. The method as claimed in claim 3, wherein said citrullinated peptide is selected from the group consisting of:
   (a) a peptide of sequence SEQ ID NO: 1 in which $X_1$, $X_2$ and $X_3$ are citrullyl residues, and
   (b) a peptide of 16 to 25 amino acids, said peptide comprising the amino acid sequence of SEQ ID NO:1, wherein $X_1$, $X_2$ and $X_3$ are citrullyl residues.

5. The method as claimed in claim 2, wherein said citrullinated peptide is selected from the group consisting of:
   a peptide defined by the sequence SEQ ID NO: 2 in which at least $X_2$ is a citrullyl residue,
   a peptide of 5 to 25 amino acids, said peptide comprising a fragment of at least 5 consecutive amino acids of the amino acid sequence of SEQ ID NO:2 containing at least one of $X_1$ or $X_2$ as a citrullyl residue, and a peptide defined by the sequence SEQ ID NO: 2 in which at least $X_1$ is a citrullyl residue.

6. The method as claimed in claim 5, wherein said citrullinated peptide is selected from the group consisting of:
   a peptide defined by the sequence SEQ ID NO: 2 in which X1 and X2 are citrullyl residues, and
   a peptide of 5 to 25 amino acids, said peptide comprising at least 5 consecutive amino acids of the amino acid sequence of SEQ ID NO:2 containing $X_1$ and $X_2$ as citrullyl residues.

7. The method as claimed in claim 6, which comprises administering a first peptide defined by the sequence SEQ ID NO: 1 in which X1, X2 and X3 are citrullyl residues, and administering a second peptide defined by the sequence SEQ ID NO: 2 in which X1 and X2 are citrullyl residues.

8. The method as claimed in claim 1, wherein the terminal carboxyl (COOH) function of said peptide is replaced with a carboxamide (CONH2) function.

* * * * *

SEQUENCE LISTING

```
<160> NUMBER OF SEQ ID NOS: 23

<210> SEQ ID NO 1
<211> LENGTH: 15
<212> TYPE: PRT
<213> ORGANISM: Artificial sequence
<220> FEATURE:
<223> OTHER INFORMATION: Citrullinated peptide
<220> FEATURE:
<221> NAME/KEY: MISC_FEATURE
<222> LOCATION: (1)..(1)
<223> OTHER INFORMATION: Xaa can be citrullyl or arginyl residue
<220> FEATURE:
<221> NAME/KEY: MISC_FEATURE
<222> LOCATION: (13)..(13)
<223> OTHER INFORMATION: Xaa can be citrullyl or arginyl residue
<220> FEATURE:
<221> NAME/KEY: MISC_FEATURE
<222> LOCATION: (15)..(15)
<223> OTHER INFORMATION: Xaa can be citrullyl or arginyl residue

<400> SEQUENCE: 1

Xaa Pro Ala Pro Pro Ile Ser Gly Gly Gly Tyr Xaa Ala Xaa
1               5                   10                  15

<210> SEQ ID NO 2
<211> LENGTH: 15
<212> TYPE: PRT
<213> ORGANISM: Artificial sequence
<220> FEATURE:
<223> OTHER INFORMATION: Citrullinated peptide
<220> FEATURE:
<221> NAME/KEY: MISC_FEATURE
<222> LOCATION: (3)..(3)
<223> OTHER INFORMATION: Xaa can be citrullyl or arginyl residue
<220> FEATURE:
<221> NAME/KEY: MISC_FEATURE
<222> LOCATION: (7)..(7)
<223> OTHER INFORMATION: Xaa can be citrullyl or arginyl residue

<400> SEQUENCE: 2

Gly Pro Xaa Val Val Glu Xaa His Gln Ser Ala Cys Lys Asp Ser
1               5                   10                  15

<210> SEQ ID NO 3
<211> LENGTH: 15
<212> TYPE: PRT
<213> ORGANISM: Artificial sequence
<220> FEATURE:
<223> OTHER INFORMATION: Citrullinated peptide
<220> FEATURE:
```

```
<221> NAME/KEY: MISC_FEATURE
<222> LOCATION: (10)..(10)
<223> OTHER INFORMATION: Xaa can be citrullyl or arginyl residue
<220> FEATURE:
<221> NAME/KEY: MISC_FEATURE
<222> LOCATION: (12)..(12)
<223> OTHER INFORMATION: Xaa can be citrullyl or arginyl residue

<400> SEQUENCE: 3

Ser Gly Ile Gly Thr Leu Asp Gly Phe Xaa His Xaa His Pro Asp
1               5                   10                  15

<210> SEQ ID NO 4
<211> LENGTH: 15
<212> TYPE: PRT
<213> ORGANISM: Artificial sequence
<220> FEATURE:
<223> OTHER INFORMATION: Citrullinated peptide
<220> FEATURE:
<221> NAME/KEY: MISC_FEATURE
<222> LOCATION: (8)..(8)
<223> OTHER INFORMATION: Xaa can be citrullyl or arginyl residue
<220> FEATURE:
<221> NAME/KEY: MISC_FEATURE
<222> LOCATION: (11)..(11)
<223> OTHER INFORMATION: Xaa can be citrullyl or arginyl residue

<400> SEQUENCE: 4

Val Asp Ile Asp Ile Lys Ile Xaa Ser Cys Xaa Gly Ser Cys Ser
1               5                   10                  15

<210> SEQ ID NO 5
<211> LENGTH: 15
<212> TYPE: PRT
<213> ORGANISM: Artificial sequence
<220> FEATURE:
<223> OTHER INFORMATION: Citrullinated peptide
<220> FEATURE:
<221> NAME/KEY: MISC_FEATURE
<222> LOCATION: (1)..(1)
<223> OTHER INFORMATION: Xaa can be citrullyl or arginyl residue
<220> FEATURE:
<221> NAME/KEY: MISC_FEATURE
<222> LOCATION: (7)..(7)
<223> OTHER INFORMATION: Xaa can be citrullyl or arginyl residue
<220> FEATURE:
<221> NAME/KEY: MISC_FEATURE
<222> LOCATION: (10)..(10)
<223> OTHER INFORMATION: Xaa can be citrullyl or arginyl residue

<400> SEQUENCE: 5

Xaa Gly His Ala Lys Ser Xaa Pro Val Xaa Gly Ile His Thr Ser
1               5                   10                  15

<210> SEQ ID NO 6
<211> LENGTH: 15
<212> TYPE: PRT
<213> ORGANISM: Artificial sequence
<220> FEATURE:
<223> OTHER INFORMATION: Citrullinated peptide
<220> FEATURE:
<221> NAME/KEY: MISC_FEATURE
<222> LOCATION: (3)..(3)
<223> OTHER INFORMATION: Xaa is a citrullyl residue
<220> FEATURE:
<221> NAME/KEY: MISC_FEATURE
<222> LOCATION: (7)..(7)
<223> OTHER INFORMATION: Xaa is a citrullyl residue

<400> SEQUENCE: 6

Gly Pro Xaa Val Val Glu Xaa His Gln Ser Ala Cys Lys Asp Ser
1               5                   10                  15
```

```
<210> SEQ ID NO 7
<211> LENGTH: 15
<212> TYPE: PRT
<213> ORGANISM: Artificial sequence
<220> FEATURE:
<223> OTHER INFORMATION: Citrullinated peptide
<220> FEATURE:
<221> NAME/KEY: MISC_FEATURE
<222> LOCATION: (8)..(8)
<223> OTHER INFORMATION: Xaa is a citrullyl residue
<220> FEATURE:
<221> NAME/KEY: MISC_FEATURE
<222> LOCATION: (11)..(11)
<223> OTHER INFORMATION: Xaa is a citrullyl residue

<400> SEQUENCE: 7

Val Asp Ile Asp Ile Lys Ile Xaa Ser Cys Xaa Gly Ser Cys Ser
1               5                   10                  15

<210> SEQ ID NO 8
<211> LENGTH: 15
<212> TYPE: PRT
<213> ORGANISM: Artificial sequence
<220> FEATURE:
<223> OTHER INFORMATION: Citrullinated peptide
<220> FEATURE:
<221> NAME/KEY: MISC_FEATURE
<222> LOCATION: (4)..(4)
<223> OTHER INFORMATION: Xaa is a citrullyl residue
<220> FEATURE:
<221> NAME/KEY: MISC_FEATURE
<222> LOCATION: (8)..(8)
<223> OTHER INFORMATION: Xaa is a citrullyl residue

<400> SEQUENCE: 8

Ser Cys Ser Xaa Ala Leu Ala Xaa Glu Val Asp Leu Lys Asp Tyr
1               5                   10                  15

<210> SEQ ID NO 9
<211> LENGTH: 15
<212> TYPE: PRT
<213> ORGANISM: Artificial sequence
<220> FEATURE:
<223> OTHER INFORMATION: Citrullinated peptide
<220> FEATURE:
<221> NAME/KEY: MISC_FEATURE
<222> LOCATION: (13)..(13)
<223> OTHER INFORMATION: Xaa is a citrullyl residue

<400> SEQUENCE: 9

Pro Glu Trp Lys Ala Leu Thr Asp Met Pro Gln Met Xaa Met Glu
1               5                   10                  15

<210> SEQ ID NO 10
<211> LENGTH: 15
<212> TYPE: PRT
<213> ORGANISM: Artificial sequence
<220> FEATURE:
<223> OTHER INFORMATION: Citrullinated peptide
<220> FEATURE:
<221> NAME/KEY: MISC_FEATURE
<222> LOCATION: (5)..(5)
<223> OTHER INFORMATION: Xaa is a citrullyl residue
<220> FEATURE:
<221> NAME/KEY: MISC_FEATURE
<222> LOCATION: (13)..(13)
<223> OTHER INFORMATION: Xaa is a citrullyl residue

<400> SEQUENCE: 10

Met Glu Leu Glu Xaa Pro Gly Gly Asn Glu Ile Thr Xaa Gly Gly
```

```
1               5                   10                  15
```

<210> SEQ ID NO 11
<211> LENGTH: 15
<212> TYPE: PRT
<213> ORGANISM: Artificial sequence
<220> FEATURE:
<223> OTHER INFORMATION: Citrullinated peptide
<220> FEATURE:
<221> NAME/KEY: MISC_FEATURE
<222> LOCATION: (2)..(2)
<223> OTHER INFORMATION: Xaa is a citrullyl residue

<400> SEQUENCE: 11

```
Glu Xaa Gly Ser Ala Gly His Trp Thr Ser Glu Ser Ser Val Ser
1               5                   10                  15
```

<210> SEQ ID NO 12
<211> LENGTH: 15
<212> TYPE: PRT
<213> ORGANISM: Artificial sequence
<220> FEATURE:
<223> OTHER INFORMATION: Citrullinated peptide
<220> FEATURE:
<221> NAME/KEY: MISC_FEATURE
<222> LOCATION: (9)..(9)
<223> OTHER INFORMATION: Xaa is a citrullyl residue

<400> SEQUENCE: 12

```
Asp Ser Pro Gly Ser Gly Asn Ala Xaa Pro Asn Asn Pro Asp Trp
1               5                   10                  15
```

<210> SEQ ID NO 13
<211> LENGTH: 15
<212> TYPE: PRT
<213> ORGANISM: Artificial sequence
<220> FEATURE:
<223> OTHER INFORMATION: Citrullinated peptide
<220> FEATURE:
<221> NAME/KEY: MISC_FEATURE
<222> LOCATION: (15)..(15)
<223> OTHER INFORMATION: Xaa is a citrullyl residue

<400> SEQUENCE: 13

```
Gly Thr Phe Glu Glu Val Ser Gly Asn Val Ser Pro Gly Thr Xaa
1               5                   10                  15
```

<210> SEQ ID NO 14
<211> LENGTH: 15
<212> TYPE: PRT
<213> ORGANISM: Artificial sequence
<220> FEATURE:
<223> OTHER INFORMATION: Citrullinated peptide
<220> FEATURE:
<221> NAME/KEY: MISC_FEATURE
<222> LOCATION: (10)..(10)
<223> OTHER INFORMATION: Xaa is a citrullyl residue
<220> FEATURE:
<221> NAME/KEY: MISC_FEATURE
<222> LOCATION: (12)..(12)
<223> OTHER INFORMATION: Xaa is a citrullyl residue

<400> SEQUENCE: 14

```
Ser Gly Ile Gly Thr Leu Asp Gly Phe Xaa His Xaa His Pro Asp
1               5                   10                  15
```

<210> SEQ ID NO 15
<211> LENGTH: 15
<212> TYPE: PRT
<213> ORGANISM: Artificial sequence

```
<220> FEATURE:
<223> OTHER INFORMATION: Citrullinated peptide
<220> FEATURE:
<221> NAME/KEY: MISC_FEATURE
<222> LOCATION: (2)..(2)
<223> OTHER INFORMATION: Xaa is a citrullyl residue

<400> SEQUENCE: 15

Ser Xaa Gly Ser Glu Ser Gly Ile Phe Thr Asn Thr Lys Glu Ser
1               5                   10                  15

<210> SEQ ID NO 16
<211> LENGTH: 15
<212> TYPE: PRT
<213> ORGANISM: Artificial sequence
<220> FEATURE:
<223> OTHER INFORMATION: Citrullinated peptide
<220> FEATURE:
<221> NAME/KEY: MISC_FEATURE
<222> LOCATION: (13)..(13)
<223> OTHER INFORMATION: Xaa is a citrullyl residue

<400> SEQUENCE: 16

Ser Ser His His Pro Gly Ile Ala Glu Phe Pro Ser Xaa Gly Lys
1               5                   10                  15

<210> SEQ ID NO 17
<211> LENGTH: 15
<212> TYPE: PRT
<213> ORGANISM: Artificial sequence
<220> FEATURE:
<223> OTHER INFORMATION: Citrullinated peptide
<220> FEATURE:
<221> NAME/KEY: MISC_FEATURE
<222> LOCATION: (4)..(4)
<223> OTHER INFORMATION: Xaa is a citrullyl residue

<400> SEQUENCE: 17

Ser Tyr Asn Xaa Gly Asp Ser Thr Phe Glu Ser Lys Ser Tyr Lys
1               5                   10                  15

<210> SEQ ID NO 18
<211> LENGTH: 15
<212> TYPE: PRT
<213> ORGANISM: Artificial sequence
<220> FEATURE:
<223> OTHER INFORMATION: Citrullinated peptide
<220> FEATURE:
<221> NAME/KEY: MISC_FEATURE
<222> LOCATION: (1)..(1)
<223> OTHER INFORMATION: Xaa is a citrullyl residue
<220> FEATURE:
<221> NAME/KEY: MISC_FEATURE
<222> LOCATION: (7)..(7)
<223> OTHER INFORMATION: Xaa is a citrullyl residue
<220> FEATURE:
<221> NAME/KEY: MISC_FEATURE
<222> LOCATION: (10)..(10)
<223> OTHER INFORMATION: Xaa is a citrullyl residue

<400> SEQUENCE: 18

Xaa Gly His Ala Lys Ser Xaa Pro Val Xaa Gly Ile His Thr Ser
1               5                   10                  15

<210> SEQ ID NO 19
<211> LENGTH: 15
<212> TYPE: PRT
<213> ORGANISM: Artificial sequence
<220> FEATURE:
<223> OTHER INFORMATION: Citrullinated peptide
<220> FEATURE:
```

```
<221> NAME/KEY: MISC_FEATURE
<222> LOCATION: (1)..(1)
<223> OTHER INFORMATION: Xaa is a citrullyl residue
<220> FEATURE:
<221> NAME/KEY: MISC_FEATURE
<222> LOCATION: (13)..(13)
<223> OTHER INFORMATION: Xaa is a citrullyl residue
<220> FEATURE:
<221> NAME/KEY: MISC_FEATURE
<222> LOCATION: (15)..(15)
<223> OTHER INFORMATION: Xaa is a citrullyl residue

<400> SEQUENCE: 19

Xaa Pro Ala Pro Pro Ile Ser Gly Gly Gly Tyr Xaa Ala Xaa
1               5                   10                  15

<210> SEQ ID NO 20
<211> LENGTH: 15
<212> TYPE: PRT
<213> ORGANISM: Artificial sequence
<220> FEATURE:
<223> OTHER INFORMATION: Citrullinated peptide
<220> FEATURE:
<221> NAME/KEY: MISC_FEATURE
<222> LOCATION: (15)..(15)
<223> OTHER INFORMATION: Xaa is a citrullyl residue

<400> SEQUENCE: 20

Gln Lys Leu Glu Ser Asp Val Ser Ala Gln Met Glu Tyr Cys Xaa
1               5                   10                  15

<210> SEQ ID NO 21
<211> LENGTH: 15
<212> TYPE: PRT
<213> ORGANISM: Artificial sequence
<220> FEATURE:
<223> OTHER INFORMATION: Citrullinated peptide
<220> FEATURE:
<221> NAME/KEY: MISC_FEATURE
<222> LOCATION: (5)..(5)
<223> OTHER INFORMATION: Xaa is a citrullyl residue
<220> FEATURE:
<221> NAME/KEY: MISC_FEATURE
<222> LOCATION: (14)..(14)
<223> OTHER INFORMATION: Xaa is a citrullyl residue

<400> SEQUENCE: 21

Val Ile Gln Asn Xaa Gln Asp Gly Ser Val Asp Phe Gly Xaa Lys
1               5                   10                  15

<210> SEQ ID NO 22
<211> LENGTH: 15
<212> TYPE: PRT
<213> ORGANISM: Artificial sequence
<220> FEATURE:
<223> OTHER INFORMATION: Citrullinated peptide
<220> FEATURE:
<221> NAME/KEY: MISC_FEATURE
<222> LOCATION: (2)..(2)
<223> OTHER INFORMATION: Xaa is a citrullyl residue

<400> SEQUENCE: 22

Pro Xaa Lys Gln Cys Ser Lys Glu Asp Gly Gly Gly Trp Trp Tyr
1               5                   10                  15

<210> SEQ ID NO 23
<211> LENGTH: 15
<212> TYPE: PRT
<213> ORGANISM: Artificial sequence
<220> FEATURE:
<223> OTHER INFORMATION: Citrullinated peptide
```

```
<220> FEATURE:
<221> NAME/KEY: MISC_FEATURE
<222> LOCATION: (4)..(4)
<223> OTHER INFORMATION: Xaa is a citrullyl residue
<220> FEATURE:
<221> NAME/KEY: MISC_FEATURE
<222> LOCATION: (13)..(13)
<223> OTHER INFORMATION: Xaa is a citrullyl residue

<400> SEQUENCE: 23

Trp Tyr Asn Xaa Cys His Ala Ala Asn Pro Asn Gly Xaa Tyr Tyr
1               5                   10                  15
```